(12) United States Patent
Mignard et al.

(10) Patent No.: US 6,217,750 B1
(45) Date of Patent: *Apr. 17, 2001

(54) PROCESS FOR PURIFYING NAPHTHALENE BY SELECTIVE HYDROTREATMENT FOLLOWED BY SEPARATION

(75) Inventors: Samuel Mignard, Chatou; Guenaël Drouglazet, Kingersheim; Slavik Kasztelan, Rueil-Malmaison; Jean Cosyns, Maule; Michel Bloch, Rueil-Malmaison; René Genin, Mulhouse, all of (FR)

(73) Assignee: Institut Francais du Petrole (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/008,582

(22) Filed: Jan. 16, 1998

(30) Foreign Application Priority Data

Jan. 20, 1997 (FR) .................................................. 97/00618

(51) Int. Cl.⁷ .......................... C10G 45/60; C10G 25/00; C10G 45/04
(52) U.S. Cl. .................. 208/213; 208/212; 208/216 PP; 208/254 H; 208/255
(58) Field of Search .................... 208/212, 213, 208/216 PP, 254 H, 255

(56) References Cited

U.S. PATENT DOCUMENTS

| | | | |
|---|---|---|---|
| 2,981,773 | * 4/1961 | Weedman | 260/707 |
| 3,277,199 | * 10/1966 | Poll | 260/674 |
| 3,394,074 | * 7/1968 | Buchmann et al. | 208/111 |
| 3,531,398 | * 9/1970 | Adams et al. | 208/216 |
| 4,267,033 | * 5/1981 | Heck et al. | 208/216 PP |
| 4,469,590 | * 9/1984 | Schucker et al. | 208/143 |
| 4,600,703 | * 7/1986 | Morales et al. | 502/210 |

FOREIGN PATENT DOCUMENTS 05 085 960   4/1993 (JP) .

OTHER PUBLICATIONS

Chemical Abstracts, vol. 119, No. 9, Abstract No. 95910m, Aug. 30, 1993.

* cited by examiner

Primary Examiner—Walter D. Griffin
Assistant Examiner—Tam M. Nguyen
(74) Attorney, Agent, or Firm—Millen, White, Zelano & Branigan, P.C.

(57) ABSTRACT

The invention concerns a process for purifying naphthalene. The process comprises selective hydrotreatment corresponding to hydrodesulphuration and/or hydrodenitrogenation and/or hydrodehydroxylation and/or hydrogenation of olefins while limiting naphthalene hydrogenation. The catalyst used comprises a matrix, at least one group VIII metal, at least one group VI metal and optionally phosphorous. It has a specific surface area of at most 220 $m^2/g$, a pore volume of 0.35–0.7 ml/g and an average pore diameter of over 10 nm. The process is carried out at 150–325° C. at a pressure of 0.1–0.9 MPa, with an HSV of 0.05–10 $h^{-1}$, and a $H_2$/naphthalene ratio of 0.1–1.3 mole/mole. The effluent, freed of $H_2S$, $NH_3$ and water, undergoes a naphthalene separation process by distillation or, as is preferable, by crystallisation. Further, recycling the separated tetralin to the hydrotreatment step can substantially increase the naphthalene yield. In this case, the tetralin/naphthalene ratio at the reactor inlet is in the range 0.005 to 0.08.

17 Claims, No Drawings

PROCESS FOR PURIFYING NAPHTHALENE BY SELECTIVE HYDROTREATMENT FOLLOWED BY SEPARATION

The invention concerns a process for purifying a naphthalene cut, generally from coal derivatives.

Coal tar distillation products include a naphthalene fraction containing essentially naphthalene but the presence of sulphur-containing products such as benzothiophene, nitrogen-containing products such as quinoline, oxygen-containing products such as phenolic derivatives, and also unsaturated hydrocarbons such as indene can also be detected, thus being a non limiting list.

Two types of naphthalene currently exist on the market. The first type is a "technical naphthalene" with a purity of over 98%. The second type is a "pure naphthalene" mainly used for synthesis and manufacture of insecticides ("Naphthalin"). Since the latter product must be completely colourless, it has to be pure. It must be over 99.95% pure and the sulphur content must be practically zero (a few ppm by weight).

The naphthalene cut which can be used in the process of the invention can contain more than 50% by weight of naphthalene, advantageously more than 75%, and most often more than 85% by weight. It also contains sulphur-containing compounds representing up to 5% by weight of sulphur but usually less than 1%, nitrogen-containing compounds in the form of quinoline, for example (up to 1% by weight), mono-olefins such as indene (up to 1% by weight but usually less than 0.5%) and oxygen-containing compounds such as phenols (up to 1% by weight but usually less than 0.5% by weight).

The present invention concerns a process for purifying a naphthalene cut, in particular a naphthalene cut from coal derivatives, to obtain a "technical naphthalene".

Some processes for treating naphthalene cuts already exist.

Japanese patent application JP-05-017,376 describes a process for low pressure (0–20 bars) hydrogenation of a naphthalene cut in which impurities are hydrogenated as well as a portion of the naphthalene and a portion of the tetralin formed.

JP-05-085,960 describes a process for purifying a naphthalene cut comprising a first hydrogenation step in the liquid phase at a low or medium pressure (0–20 bars), at 100–300° C., using a catalyst selected from the group formed by Ni—Co—Mo, platinum on coal, Pt—Ni—Mo, Pd-alumina, or CoMo-alumina catalysts. In a second step, the effluent obtained is degassed to eliminate $H_2S$, $NH_3$ and ethylbenzene. Then the effluent is washed with an inorganic acid (third step) and then separated (fourth step). The effluent obtained is dehydrated by azeotropic distillation with ethylbenzene (fifth step). The residual impurities are adsorbed (sixth step) on clay. The effluent can then be distilled (seventh step) and pressed (eighth step) to obtain purified naphthalene.

We have sought a process for treating naphthalene cuts which is simple to carry out, in contrast to JP-05-085,960 which requires numerous treatment steps, and which can produce higher naphthalene yields than in JP-05-017,376.

The proposed invention is based on the use of a particular catalyst which can carry out prior deep hydrotreatment of the feed to eliminate the major portion of the sulphur-containing, nitrogen-containing, oxygen-containing and olefinic impurities in a single step while limiting hydrogenation (reduction in the quantity of tetralin and decalin) which constitutes selective hydrotreatment so as to be able to separate purified naphthalene simply by crystallisation. More precisely, the invention provides a process for treating a naphthalene cut containing sulphur-containing and/or nitrogen-containing and/or oxygen-containing and/or olefinic impurities in which, in a first step, the naphthalene cut is brought into contact in the presence of hydrogen with a catalyst containing at least one matrix, at least one group VIII element and at least one group VI element. It is characterized in that the catalyst used in the first step contains 5–40% by weight of oxides of metals from groups VIII and VI, with a ratio of the oxide of the group VI metal to the oxide of the group VIII metal which is in the range 1.25 to 20 by weight, said catalyst having a BET specific surface area of at most 220 $m^2/g$, a pore volume which is in the range 0.35 to 0.7 ml/g and an average pore diameter of at least 10 nm, and in that the naphthalene cut is brought into contact with the catalyst at a temperature of 150–325° C., at a total pressure of 0.1 MPa–0.9 MPa, at an hourly space velocity of 0.05–10 $h^{-1}$ and with a hydrogen/naphthalene molar ratio which is in the range 0.1 to 1.3, such that the tetralin yield is less than 10% by weight and in a second step, at least a portion of the effluent from the first step is separated from $H_2S$, $NH_3$ and water, and in a third step, at least a portion of the effluent from the second step undergoes treatment to separate naphthalene and tetralin from the effluent. If the tetralin is recycled, the tetralin/naphthalene ratio is in the range 0.005 to 0.08 by weight.

The process comprises three successive steps. The first step is intended to reduce the sulphur content present in the form of sulphur-containing molecules to the desired value. The sulphur-containing molecules are transformed into desulphurised molecules and $H_2S$. In this first step, nitrogen-containing molecules are mainly transformed into denitrogenated molecules and $NH_3$. It can also hydrogenate olefinic molecules and dehydroxylate molecules containing an OH group. During this step, the catalyst and the operating conditions are selected so as to carry out deep hydrotreatment while limiting hydrogenation of naphthalene to tetralin. The tetralin can be considered to be a by-product of the reaction which is thus unwanted. Practically no tetralin is formed (generally less than 5% by weight in the effluents, preferably less than 3%). The term "deep hydrotreatment" means at least 70% desulphurisation, preferably at least 90%, and more preferably at least 98% desulphurisation, at least 50% denitrogenation, preferably at least 80% denitrogenation, at least 80% olefin hydrogenation, preferably at least 95% hydrogenation, and at least 75% dehydroxylation, preferably at least 90% dehydroxylation.

The total pressure is in the range 0.1 MPa (1 bar) to 0.9 MPa (9 bars), preferably in the range 0.2 MPa (2 bars) to 0.9 MPa (9 bars)) and more preferably in the range 0.2 MPa (2 bars) to 0.8 MPa (8 bars). The reaction temperature is in the range 150° C. to 325° C., preferably 200° C. to 320° C., more preferably in the range 220° C. to 300° C. The hourly space velocity (HSV) is in the range 0.05 $h^{-1}$ to 10 $h^{-1}$, preferably in the range 0.1 $h^{-1}$ to 5 $h^{-1}$ and more preferably in the range 0.15 $h^{-1}$ to 2 $h^{-1}$. The hydrogen/naphthalene molar ratio at the reactor inlet is in the range 0.1 to 1.3, more preferably less than 1.

The catalyst used for the first hydrotreatment step is a catalyst containing at least one matrix, advantageously based on alumina, preferably containing no zeolite, and at least one metal having a hydro-dehydrogenating function. The matrix can also comprise a silica-alumina, boron oxide, magnesia, zirconia, clay or a combination of these oxides. The hydro-dehydrogenating function is assured by a combination of at least one group VIII metal or metal compound, in particular nickel or cobalt, and at least one metal or metal compound (in particular molybdenum or tungsten) from group VI of the periodic table. The total concentration of oxides of group VI and VIII metals is in the range 5% to 40% by weight, preferably in the range 7% to 30% by weight, and the weight ratio (expressed as the metallic oxide of the metal) (or metals) from group VI over the group VIII metal (or metals) is in the range 1.25 to 20, preferably in the range 2 to 10. Further, the catalyst can preferably contain phosphorous. The phosphorous content, expressed as the concentration of phosphorous oxide $P_2O_5$, is below 15% by weight, preferably less than 10% by weight.

The preferred catalyst is of the type CoMo deposited on alumina.

The catalyst has very particular characteristics:

The BET specific surface area is at most 220 $m^2/g$, or below 200 $m^2/g$ when the catalyst contains phosphorous, and in that case the preferred surface area is at most 180 $m^2/g$;

The pore volume is in the range 0.35 to 0.7 ml/g;

The average pore diameter is at least 100 Å (10 nm), preferably in the range 100 to 200 Å, which means that the fraction of the pore volume corresponding to pores with a diameter of less than 90 Å is low (0–15%).

Before passing to the third step, at least a portion of the effluent which has undergone hydrotreatment will be practically freed, either completely or partially (at least 95% and preferably, at least 99%) of the $H_2S$, $NH_3$ and $H_2O$ water molecules which have been generated. Any method which can carry out such separations can be used. Normally, a simple stripping column is used.

The third step is intended to recover the major portion of the naphthalene with the highest possible purity. Any separation method is possible, for example distillation. The naphthalene purity is thus of the order of 99.6%. Higher purity (for example over 99.96%) can be obtained, a melt purification process is of particular advantage, in particular the PROAB® process sold by BEFS PROKEM. The process and apparatus for purifying any crystallisable product are described in French patent FR-A-2 493 172. The apparatus, which has subsequently been improved upon (European patent application EP-A-0 728 508) is highly advantageous for this type of purification. The disclosures of these patents are included in the present description. This third step is essentially intended to separate pure naphthalene from tetralin and other impurities contained in the effluent from the preceding step.

The crystallisation process can separate the mixture obtained after hydrogenation and stripping. The process, which is highly efficient as regards the components constituting impurities of pure naphthalene, can produce a high purity. It is used alone, in contrast to other current processes where a combination of 2, 3 or more different processes are required to achieve the high purity shown in Table 3, for example distillation then acid extraction, clay treatment, evaporation.

It may be advantageous to precede the crystallisation step with a distillation step, in which case the process is carried out in four steps.

The crystallisation process can use techniques for washing the pure naphthalene crystals either by fractional melting or by washing using a portion of the purified product which is supplied to the purification process as a counter-current.

The stripped effluent undergoes crystallisation as follows: the crystallisation operations are carried out in a completely automatic apparatus without any manual intervention. A fluid circulates in the apparatus. Depending on the phase of the process, this fluid is alternately heated or cooled using heat exchangers. Fine regulation means that exact amounts of heat can be supplied to or withdrawn from the naphthalene as required by the operation. The crude naphthalene, which has been melted before being introduced into one of the crystallisers, undergoes freezing under inert atmosphere, which causes highly controlled crystallisation of the product. As it cools, the quantity of crystals increases to a certain predetermined level; solid and liquid are then separated by draining. In order to continue purification of the crystals, the procedure is as follows:

Either partial melting of the crystals (sweating). On melting, the crystals generate pure naphthalene which mixes with the residual liquid film and purifies it;

or washing, consisting of sequences of filling/emptying the apparatus using liquids of increasing in purity.

The pure residual crystals are then completely melted and the apparatus is emptied. Depending on the efficiency of the crystallisation process selected and the desired final purity, one or more crystallisation stages can be used.

In general, the melt crystallisation process is carried out at temperatures which are in the range 60–90° C., preferably in the range 75–85° C. by crystallising naphthalene in filled or partly filled vessels. It can be carried out dynamically, for example by circulating the product to be crystallised inside tubes or by trickling a film inside or outside the tubes. It can also be carried out statically, for example using a space filled with product to be crystallised provided with heat transfer elements immersed in the product.

Performances of the crystallisation process: the melt crystallisation process can produce high naphthalene purities (99–99.999%), more generally over 99.90%.

The tetralin yield is normally below 10% by weight, preferably less than 5% by weight, more preferably 3% by weight or less (the yield is the mass of tetralin formed with respect to the mass of naphthalene at the hydrotreatment reactor outlet).

In order to increase the naphthalene yield, it is also possible to recycle the tetralin, i.e., to add all or a portion of the tetralin recovered after the separation stage to the starting feed. The quantity of tetralin introduced is in a tetralin/naphthalene weight ratio which is in the range 0.005 to 0.08.

Our research has led to the surprising discovery that a sequence of selective deep hydrotreatment and separation can produce high purity naphthalene in a very high yield.

The following examples illustrate the invention without in any way limiting its scope.

They were carried out using a coal derivative type naphthalene feed; its analysis is shown in Table 1.

TABLE 1

|  | Content (weight %) |
|---|---|
| Benzothiophene | 2.45 |
| i.e., sulphur | i.e. 0.586 |
| Naphthalene | 96.5 |
| Tetralin | 0 |
| Phenols | 0.3 |
| Indene | 0.15 |
| 1 and 2-methyl-naphthalene | 0.2 |
| Quinoline | 0.3 |

EXAMPLE 1

Hydrotreatment (HDT) then Stripping and Crystallisation

The feed was purified by deep selective hydrotreatment followed by stripping then by distillation.

The hydrotreatment operating conditions were as follows: temperature: 318° C.; total pressure: 0.5 MPa (5 bars); hydrogen flow rate: 125 l/l, i.e., a molar ratio of 0.62; and HSV: 1 $h^{-1}$.

The catalyst contained 3% by weight of CoO and 14% by weight of $MoO_3$ deposited on alumina. The specific surface area of the catalyst was 210 $m^2/g$; its average pore diameter was 10 Å and the pore volume was 0.58 ml/g.

All of the effluent was stripped to eliminate $H_2S$, $NH_3$ and $H_2O$ as gases. Completely hydrogenated indene remained in the effluent.

Table 2 shows the analysis of the effluent obtained after hydrotreatment and stripping. The effluent obtained after stripping was then crystallised as described above in a static PROABD® type crystalliser by partial melting of the crystals to purify the naphthalene. Molten naphthalene was introduced into the crystalliser. The temperature of the latter was then dropped to cause controlled crystallisation of the product. Crystallisation was interrupted when the product temperature reached 66° C., to drain off the mother liquor. After draining, the crystals were partially melted by raising the temperature to 78.5° C. The product was then completely melted. In order to obtain a final purity of 99.96%, a second crystallisation purifying stage was required. It comprised the same operations as described above, but the operating temperatures were different:

crystallisation to 78° C. then draining off the mother liquors;

partial melting of crystals to 79.8° C.;

complete melting of the purified product.

Table 2 also shows an analysis of the effluent obtained after hydrotreatment then stripping then crystallisation.

TABLE 2

|  | HDT + stripping | HDT + stripping + crystallisation |
|---|---|---|
| Sulphur (ppm by weight) | 23 | 10 |
| Naphthalene (wt %) | 97.0 | 99.960 |
| Tetralin (wt %) | 2.7 | 0.025 |
| Decalin (wt %) | 0.05 | <0.001 |
| Phenols (wt %) | <0.001 | <0.001 |
| Indene (wt %) | <0.001 | <0.001 |
| 1&2-methyl-naphthalene (wt %) | 0.20 | 0.005 |
| Quinoline (wt %) | 0.10 | 0.004 |
| Melting point (° C.) | 78 | >80.2 |

Using selective hydrotreatment and crystallisation produced a very good quality product. The sulphur content was reduced to 10 ppm by weight which corresponded to over 99.8% hydrodesulphuration. Being 99.6% pure and having a melting point of more than 80.2° C., the naphthalene obtained was a "pure naphthalene" type.

EXAMPLE 2

Using a Recycle

In the preceding example, the final product contained practically no tetralin as this had been eliminated during the crystallisation step. The separated tetralin was practically entirely recycled to the reactor inlet which improved the naphthalene yield as shown in Table 3.

Table 3 shows the results obtained with and without tetralin recycling, the process being carried out as in Example 1. The residue fraction corresponded to the fraction which was not naphthalene and which was recovered during the crystallisation step.

TABLE 3

|  |  | Without recycling | With recycling |
|---|---|---|---|
| Reactor inlet: | Feed A | 100 | 97 |
|  | Tetralin | 0 | 3 |
| Crystallisation outlet: | Naphthalene yield | 97 | 96.5 |
|  | Naphthalene purity | 99.96 | 99.96 |
|  | Tetralin yield | 3.0 | 0.5 |
| Naphthalene yield | (outlet/inlet) | 97% | 99.5% |

With no recycling, the naphthalene yield was 97%. When recycling was used, the naphthalene yield was then 99.5%. The naphthalene yield was thus substantially improved. 3.5% of tetralin was recovered. About 0.5% was purged and only 3.0% was recycled. The purge, which was not obligatory, had the effect of maintaining the purity of the naphthalene at a very high level.

What is claimed is:

1. A process for treating a naphthalene cut containing sulphur-containing and/or nitrogen-containing and/or oxygen-containing and/or olefinic impurities, in which, in a first step, the naphthalene cut is brought into contact in the presence of hydrogen with a catalyst containing at least one matrix, at least one group VIII element, phosphorous and at least one group VI element, said process being characterized in that:

a) the catalyst used in the first step contains 5–40% by weight of oxides of metals from groups VIII and VI, and less than 15% by weight phosphorous, expressed as $P_2O_5$ with a ratio of the oxide of the group VI metal to the oxide of the group VIII metal which is in the range 1.25 to 20 by weight, said catalyst having a BET specific surface area of at most 220 $m^2/g$, a pore volume which is in the range 0.35 to 0.7 ml/g and an average pore diameter of at least 10 nm, and in that the naphthalene cut is brought into contact with said catalyst at a temperature of 150–325° C., at a total pressure of 0.1 MPa—MPa, at an hourly space velocity of 0.05–10 $h^{-1}$ and with a hydrogen/naphthalene molar ratio which is in the range 0.1 to 1.3, such that the yield of tetralin is less than 10% by weight; and b) in a second step, at least a portion of the effluent from the first step is separated from $H_2S$, $NH_3$ and water; and c) in a third step, at least a portion of the effluent from the second step undergoes treatment to separate naphthalene and tetralin from said effluent, wherein at least a portion of the tetralin separated in the third step is recycled to the first step in a tetralin/naphthalene weight ratio of 0.005 to 0.08.

2. A process according to claim 1, characterized in that the third step comprises a crystallisation step.

3. A process according to claim 1, characterized in that the third step comprises a distillation step followed by final purification by melt crystallisation.

4. A process according to claim 1, characterized in that the catalyst in the first step comprises at least one matrix selected from the group consisting of alumina, silica-alumina, boron oxide, magnesia, zirconia, clay, and at least one group VIII metal selected from the group consisting of cobalt and nickel, and at least one group VI metal selected from the group consisting of molybdenum and tungsten.

5. A process according to claim 1, characterized in that the BET specific surface area of the catalyst is at most 180 m$^2$/g.

6. A process according to claim 1, characterized in that the average pore diameter is 10–20 nm.

7. A process according to claim 1, characterized in that the second step is a stripping step.

8. A process according to claim 1, characterized in that the melt crystallisation step is carried out at temperatures which are in the range 60–90° C. to obtain a naphthalene purity of over 99.90%.

9. A process for treating a naphthalene cut containing sulphur-containing and/or nitrogen-containing and/or oxygen-containing and/or olefinic impurities, in which, in a first step, the naphthalene cut is brought into contact in the presence of hydrogen with a catalyst containing at least one matrix, at least one group VIII element, and at least one group VI element, said process being characterized in that:

a) the catalyst used in the first step contains 5–40% by weight of oxides of metals from groups VIII and VI, with a ratio of the oxide of the group VI metal to the oxide of the group VIII metal which is in the range 1.25 to 20 by weight, said catalyst having a BET specific surface area of at most 220 m$^2$/g, a pore volume which is in the range 0.35 to 0.7 ml/g and an average pore diameter of at least 10 nm, and in that the naphthalene cut is brought into contact with said catalyst at a temperature of 150–325° C., at a total pressure of 0.1 MPa—MPa, at an hourly space velocity of 0.05–10 h$^{-1}$ and with a hydrogen/naphthalene molar ratio which is in the range 0.1 to 1.3, such that the first is a single step, the yield of tetralin is less than 10% by weight, and at least 98% hydrosulfurization is obtained; and b) in a second step, at least a portion of the effluent from the first step is separated from H$_2$S, NH$_3$ and water; and c) in a third step, at least a portion of the effluent from the second step undergoes treatment to separate naphthalene and tetralin from said effluent, wherein at least a portion of the tetralin separated in the third step is recycled to the first step in a tetralin/naphthalene weight ratio of 0.005 to 0.08.

10. A process according to claim 9, characterized in that at least a portion of the tetralin separated in the third step is recycled to the first step in a tetralin/naphthalene weight ratio of 0.005 to 0.08.

11. A process according to claim 9, characterized in that the catalyst in the first step comprises at least one matrix selected from the group consisting of alumina, silica-alumina, boron oxide, magnesia, zirconia, clay, and least one group VIII metal selected from the group consisting of cobalt and nickel, and at least one group VI metal selected from the group consisting of molybdenum and tungsten.

12. A process according to claim 9, characterized in that the catalyst used in the first step also contains phosphorous.

13. A process according to claim 9, characterized in that the BET specific surface area of the catalyst is at most 180 m$^2$/g.

14. A process according to claim 9, characterized in that the average pore diameter is 10–20 nm.

15. A process according to claim 12, characterized in that the phosphorous content is below 15% by weight, expressed as P$_2$O$_5$.

16. A process according to claim 1 wherein the fraction of pore volume provided by pores having a diameter less than 90 Å is from 0–15%.

17. A process according to claim 9 wherein the fraction of pore volume provided by pores having a diameter less than 90 Å is from 0–15%.

* * * * *